US008941836B2

(12) United States Patent
Gaucel et al.

(10) Patent No.: US 8,941,836 B2
(45) Date of Patent: Jan. 27, 2015

(54) METROLOGY SYSTEM AND METHOD APPLIED TO AN INTERFEROMETER FOR REMOTELY ANALYSING A GASEOUS COMPOUND

(75) Inventors: Jean-Michel Gaucel, Mandelieu la Napoule (FR); Didier Miras, Mandelieu la Napoule (FR)

(73) Assignee: Thales, Neuilly sur Seine (FR)

( * ) Notice: Subject to any disclaimer, the term of this patent is extended or adjusted under 35 U.S.C. 154(b) by 207 days.

(21) Appl. No.: 13/421,736

(22) Filed: Mar. 15, 2012

(65) Prior Publication Data

US 2013/0044327 A1   Feb. 21, 2013

(30) Foreign Application Priority Data

Mar. 17, 2011 (FR) ...................... 11 00801

(51) Int. Cl.
*G01J 3/45* (2006.01)
*G01J 3/453* (2006.01)
*G01N 21/3504* (2014.01)
*G01N 21/17* (2006.01)
*G01N 21/35* (2014.01)

(52) U.S. Cl.
CPC ........... *G01J 3/4535* (2013.01); *G01N 21/3504* (2013.01); *G01N 2021/1795* (2013.01); *G01N 2021/3595* (2013.01)
USPC ....................................... 356/451

(58) Field of Classification Search
CPC ......... G01J 3/45; G01J 3/4535; G01J 3/4531; G01J 2003/4538; G01N 2021/3595; G01B 9/0207; G01B 9/02071; G01B 9/02072; G01B 9/02079
USPC .................................. 356/451–456
See application file for complete search history.

(56) References Cited

U.S. PATENT DOCUMENTS

| 4,444,501 A   | 4/1984  | Schwiesow |
|---|---|---|
| 4,529,317 A * | 7/1985  | Cramp ............................ 356/407 |
| 5,270,790 A * | 12/1993 | Matsumura ..................... 356/452 |
| 5,546,185 A * | 8/1996  | Okumura et al. .............. 356/452 |
| 5,657,122 A * | 8/1997  | Curbelo et al. ................ 356/452 |
| 5,671,047 A * | 9/1997  | Curbelo .......................... 356/452 |

OTHER PUBLICATIONS

Peter R. Griffiths et al., "Fourier Transform Infrared Spectrometry: Tilt-Compensated Interferometers", 2007, pp. 112-123, second edition, Wiley.

* cited by examiner

*Primary Examiner* — Tarifur Chowdhury
*Assistant Examiner* — Jonathon Cook
(74) *Attorney, Agent, or Firm* — Baker & Hostetler LLP

(57) ABSTRACT

In the field of Fourier transform interferometry and in particular a device and a method for improving the precision of such a device for remotely analyzing a gaseous compound, a Fourier transform interferometer includes: at least one movable retroreflector; a metrology subsystem using at least three laser beams; and a metrology unit generating, for each sounding point represented by a pixel on the capture matrix imaging a gaseous compound, a metrology signal incorporating the displacements in space of the movable element(s).

6 Claims, 8 Drawing Sheets

METROLOGY SYSTEM AND METHOD APPLIED TO AN INTERFEROMETER FOR REMOTELY ANALYSING A GASEOUS COMPOUND

FIELD OF THE INVENTION

The present invention falls within the field of Fourier transform interferometry and relates in particular to a device and a method for improving the precision of such a device for remotely analysing a gaseous compound. The present invention applies notably to Fourier transform interferometer-imagers.

BACKGROUND

Instruments for the remote chemical and physical analysis of a gaseous compound make it possible to probe atmospheric layers. An instrument for chemically and physically analysing a gaseous compound may be applicable in the fields of metrology and the analysis of atmospheric pollutants. The present invention may be applied to a Michelson interferometer and in general to two arm interferometers using retroreflectors, for example corner cubes.

To satisfy the scientific requirements, these instruments must provide a metrology precision of the order of one nanometer. The metrology reading makes it possible to link a capture at a measurement point to an optical path difference. However, with standard metrology systems, any undesirable displacement of the movable element results in metrology errors. At such a level of precision, one of the consequences is that the constraints on the displacement mechanism of the movable element become very great.

Added to these metrological requirements is a desire to reduce the spectral resolution of the measurement, which leads, mechanically, to increasing the travel of the movable retroreflectors and correspondingly increases the difficulty of producing the mechanism.

Another requirement may be to increase the field of view in the interferometer. The field of view is the solid angle under which the gaseous component to be analysed is seen. This increase in the field increases the sensitivity of the metrology with respect to controlling the path of the movable element.

Again, the use of a Fourier transform spectrometer-imager with small pixels considerably increases, notably by a factor of one hundred, this metrology sensitivity.

Again, for the purpose of reducing the cost, volume, weight and consumed power of the interferometer, unilateral capture, that is to say restricting the capture to positive optical path differences, may be preferred. Even though this reduces the travel of the movable element by practically one half, unilateral capture considerably further increases the sensitivity of the metrology with respect to controlling the path of the movable reflector(s).

One of the consequences is that the mechanism(s) for displacing the movable element are over-constrained compared with those of interferometers of previous generations. At worst, this accumulation of mechanical constraints makes it impossible to construct the interferometer, while at best it considerably increases the design costs of the interferometer, making it impossible to reutilize the mechanisms of older generations or even to throw into question all the interferometers used in preceding generations.

This metrology precision is currently solved by injecting a laser signal having a very stable absolute wavelength into the interferometer. This injection is generally carried out at the centre of the field of view, as this position makes it possible to have an apparent wavelength which is stable with respect to the laser injection. By measuring the laser signal interference output by the interferometer it is possible to link the instant of measurement to an optical path difference, thus creating a metrology signal. In theory, if the displacement of the movable element is sufficiently close to the control, a metrology at the centre of the field of view may be used in any field. However, this single measurement at the centre of the field is no longer valid for points remote from the centre of the field whenever the constraints on the mechanism for displacing the movable element can no longer be satisfied.

A first solution may be to use a laser for metrology per measurement point, that is to say per pixel of the capture matrix or sensor. Even though this first solution does offer the desired levels of precision, it becomes unrealizable with a large number of measurement points.

A second solution uses an interpolation in the field of view of a number K, greater than three, of laser measurements. This solution requires a complex digital processing so as to obtain the required precision. In addition, this solution, like the first one, does not make it possible to have a sufficiently stable apparent wavelength so as to decorrelate a laser injection error from a shift in the interferometer axis. The position of the interferometer axis is in fact a parameter necessary for spectral calibration of the data.

A third solution, using a direct measurement of the position of the movable element, is a solution which is complicated to implement and does not make it possible to obtain real-time measurements.

SUMMARY OF THE INVENTION

One object of the invention is notably to alleviate the aforementioned drawbacks. For this purpose, one subject of the invention is a metrology system applied to an interferometer for remotely analysing a gaseous compound by Fourier transform spectroscopy. The interferometer is a two-arm interferometer, comprising at least one movable retroreflector.

The interferometer also comprises:
an injection subsystem for injecting at least three metrology laser beams into the interferometer;
a capture subsystem for receiving at least three metrology laser beams output by the interferometer, said capture subsystem delivering at least three laser signals each representing a measurement of the interference of one metrology laser beam after it has passed through the interferometer; and
at least one metrology unit which, from the laser signals, generates synthetic metrology signals for various points in a field of view of the interferometer, the synthetic metrology signals thus generated taking into account the path of the movable retroreflector or retroreflectors in space and said metrology unit including a metrology calculation component which estimates, for each received laser beam, absolute optical path differences.

In one particularly advantageous embodiment, the injection subsystem can inject at least three laser beams, one of the three laser beams being injected into the centre of the field of view of the interferometer.

The metrology unit may comprise at least:
three metrology calculation units, each calculating a raw metrology signal from a laser signal;
a unit for the generation of one synthetic metrology reading per measurement point, generating, from at least three raw metrology signals, one synthetic metrology signal per measurement point in the field of view of the interferometer.

The metrology calculation unit may perform at least the following processing steps:
  correction of the laser signal: correction of the differences in amplitude, phase and offset;
  determination of a path difference associated with the laser signal.

The unit for the generation of one synthetic metrology reading per measurement point may perform at least the following processing steps:
  estimation of a vector apex joining the positions of the vertices of the movable retroreflectors;
  elimination of the linear component of the vector apex; and
  generation of an optical path difference represented by a synthetic metrology signal, at different points in the field of view, from the vector apex and from the angular coordinates of the various points in the field of view.

Another subject of the invention is a method of metrology applied to an interferometer for remotely analysing a gaseous compound by Fourier transform spectroscopy, said interferometer being a two-arm interferometer, including at least one movable retroreflector, the method comprises at least the following steps:
  a step of injecting at least three metrology laser beams into the interferometer, performed by an injection subsystem;
  a step of receiving at least three laser metrology beams output by the interferometer, performed by a capture subsystem;
  a step of generating at least three laser signals, each representing a measurement of the interference of a metrology laser beam after it has passed through the interferometer, performed by the capture subsystem; and
  a step of generating synthetic metrology signals by at least one metrology unit from the laser signals for various points in a field of view of the interferometer, the synthetic metrology signals thus generated taking into account the path of the movable retroreflector or retroreflectors in space, the step of generating synthetic metrology signals comprising an estimation, for each received laser beam of absolute optical path differences, performed by a metrology calculation component forming part of the metrology unit.

Advantageously, one of the three laser beams may be injected into the centre of the field of view of the interferometer.

The step of generating synthetic metrology signals may comprise at least:
  calculation of a raw metrology signal from a laser signal by each of the three metrology calculation units that form parts of the metrology unit; and
  generation, from at least three raw metrology signals, of one synthetic metrology signal per measurement point in the field of view of the interferometer, by a unit for the generation of one synthetic metrology reading per measurement point.

The calculation of a raw metrology signal may comprise at least the following processing steps:
  correction of the laser signal: correction of the differences in amplitudes, phase and offset; and
  determination of a path difference associated with the laser signal.

The generation of one synthetic metrology reading per measurement point may comprise at least the following processing steps:
  estimation of a vector apex joining the positions of the vertices of the movable retroreflectors;
  elimination of the linear component of the vector apex; and
  generation of an optical path difference represented by a synthetic metrology signal, at different points in the field of view, from the vector apex and from the angular coordinates of the various points in the field of view.

One of the main advantages of the invention is to provide a metrology capable of estimating and integrating the imperfect path in space of the movable elements of the interferometer in the measurement carried out by the interferometer.

BRIEF DESCRIPTION OF THE DRAWINGS

Other features and advantages of the invention will become apparent from the following description, given by way of non-limiting illustration and in conjunction with the appended drawings which show.

DETAILED DESCRIPTION

Figure 1:
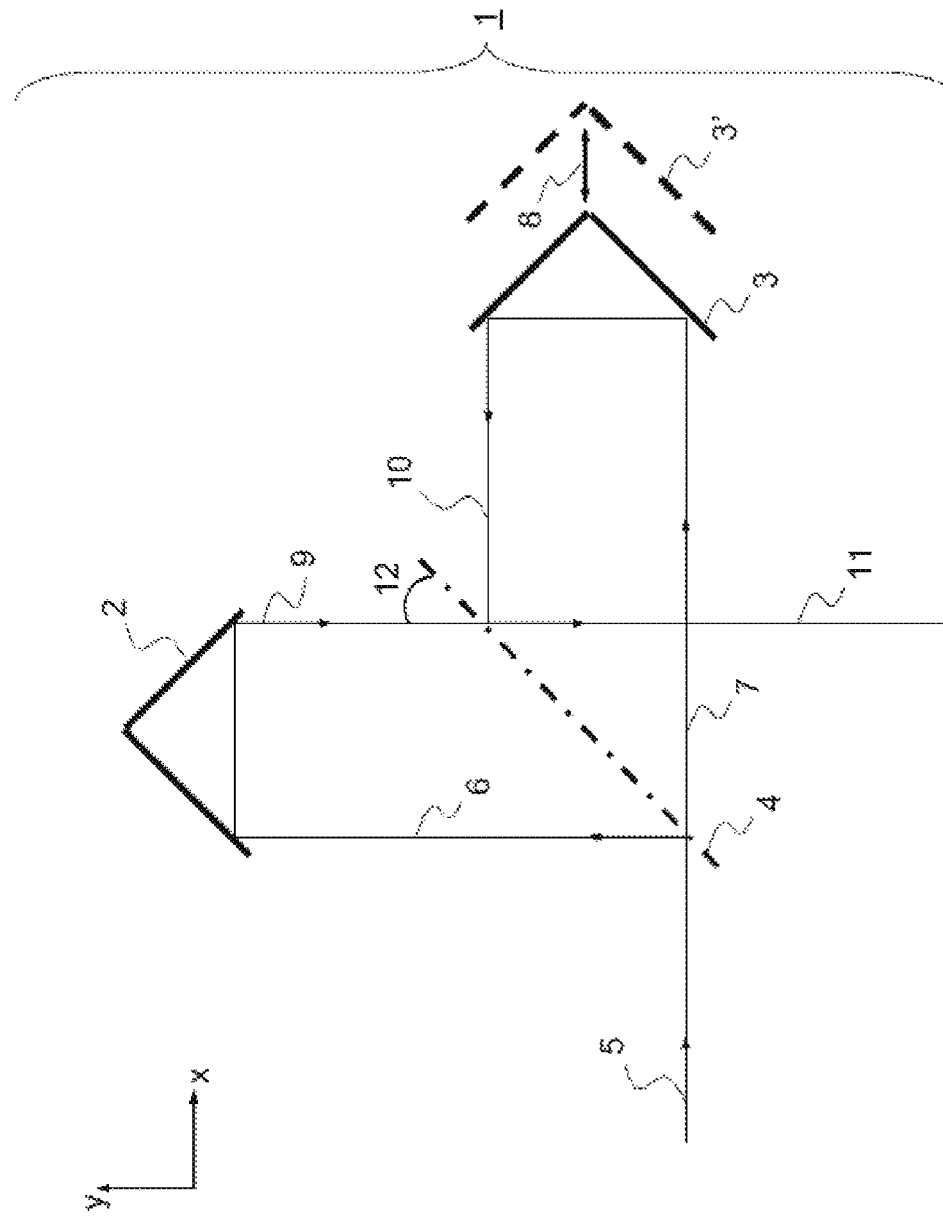
FIG. 1, schematically a first corner-cube Michelson interferometer, one corner cube of which is movable.

FIG. 1 shows schematically a first Michelson interferometer 1 according to the prior art. The interferometer shown in FIG. 1 includes a first movable retroreflector 3. This first interferometer notably includes a beam splitter/compensator plate 4. The beam splitter/compensator plate 4 notably makes it possible to split an incoming beam 5 into two beams 6, 7: a first beam 6 may be returned via a second retroreflector 2, while a second beam 7 may be returned via the first movable retroreflector 3. The first and second retroreflectors 2, 3 may be corner cubes. The first movable retroreflector 3 may be displaced linearly, for example along a first axis 8 substantially parallel to the incoming beam 5. The first axis 8 serves to define a second axis x and a third axis y substantially perpendicular to the second axis x. A plane, defined by the second and third axes x and y may be a plane (x,y) in which the first and second retroreflectors 3, 2 lie. A position 3' represents an example of a second position of the first retroreflector 3 after a displacement thereof. The first and second beams 6, 7 are reflected by the second and first retroreflectors 2, 3 respectively, in the form of third and fourth beams 9, 10 respectively. The third and fourth beams 9, 10 are then recombined by the beam splitter/compensator plate 4 in the form of an outgoing beam 11. The mean angle of incidence 12 of the first interferometer 1 is notably an anticlockwise angle between the beam splitter/compensator plate 4 and the fifth beam 9. The mean angle of incidence 12 may be between 20° and 45°. In FIG. 1, the mean angle of incidence 12 is about 45°.

Figure 2:
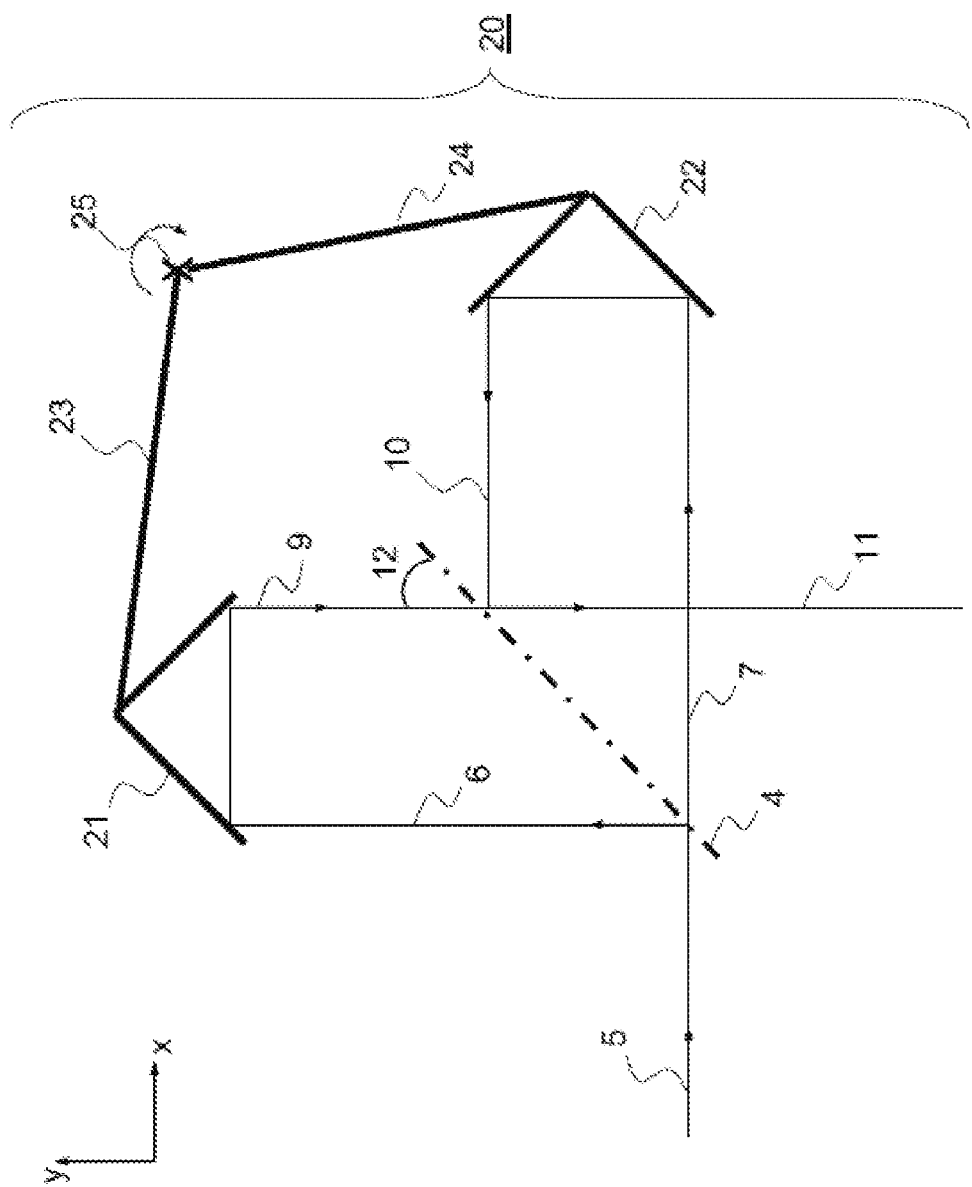
FIG. 2, schematically a second corner-cube interferometer, the two corner cubes of which are movable.

FIG. 2 shows schematically a second interferometer 20 with movable retroreflectors 21, 22 according to the prior art. The second interferometer 20 is called a "double-pendulum" interferometer. Specifically, the third and fourth movable retroreflectors 21, 22 may each be mechanically linked to a first end of a rod 23, 24, for example a rigid rod. The two rods 23, 24 are linked together by a linkage 25 at the second ends thereof. The linkage 25 may be such that the rods 23, 24 can rotate about the linkage 25. The linkage 25 may therefore be a pivot pin for the rods 23, 24. The linkage 25 may be located notably in the extension of the beam splitter/compensator plate 4. The rotation of the rods 23, 24 may notably take place in a plane defined by the third and fourth reflectors 21, 22 of the second interferometer 20. The angle between the two rods 23, 24 may notably be a fixed angle. Functionally, the beams 5, 6, 7, 10, 11 shown in FIG. 2 are the same as the beams 5, 6, 7, 10, 11 shown in FIG. 1. The angle 12 shows, as in FIG. 1, the mean angle of incidence.

Figure 3:
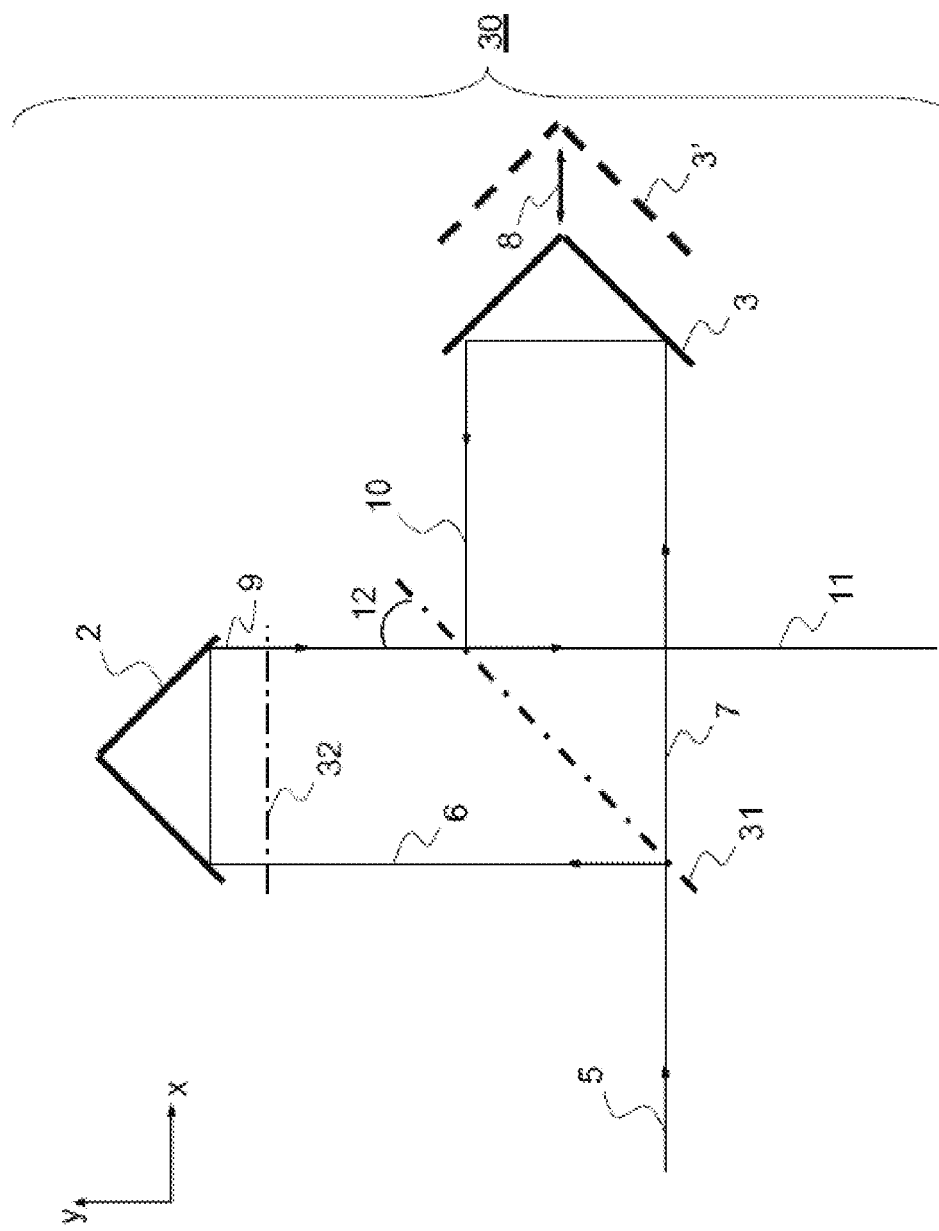
FIG. 3, schematically the first interferometer with a compensator plate offset with respect to the beam splitter plate.

FIG. 3 shows schematically a third interferometer 30 according to the prior art. The third interferometer 30 includes a beam splitter plate 31 and an offset compensator plate 32. For example, as shown in FIG. 3, the offset compensator plate 32 may be integrated with an interferometer such as the first interferometer 1. The compensator plate 32 may be offset in front of the second retroreflector 2 so that the first and third beams 6, 9 pass substantially perpendicularly therethrough. In the third interferometer 30, the various components 2, 3, 31, 32 lie in the same plane (x,y) as shown in FIG. 1. Functionally, the beams 5, 6, 7, 10, 11 shown in FIG. 3 are the same as the beams 5, 6, 7, 10, 11 shown in FIG. 1.

Figure 4:
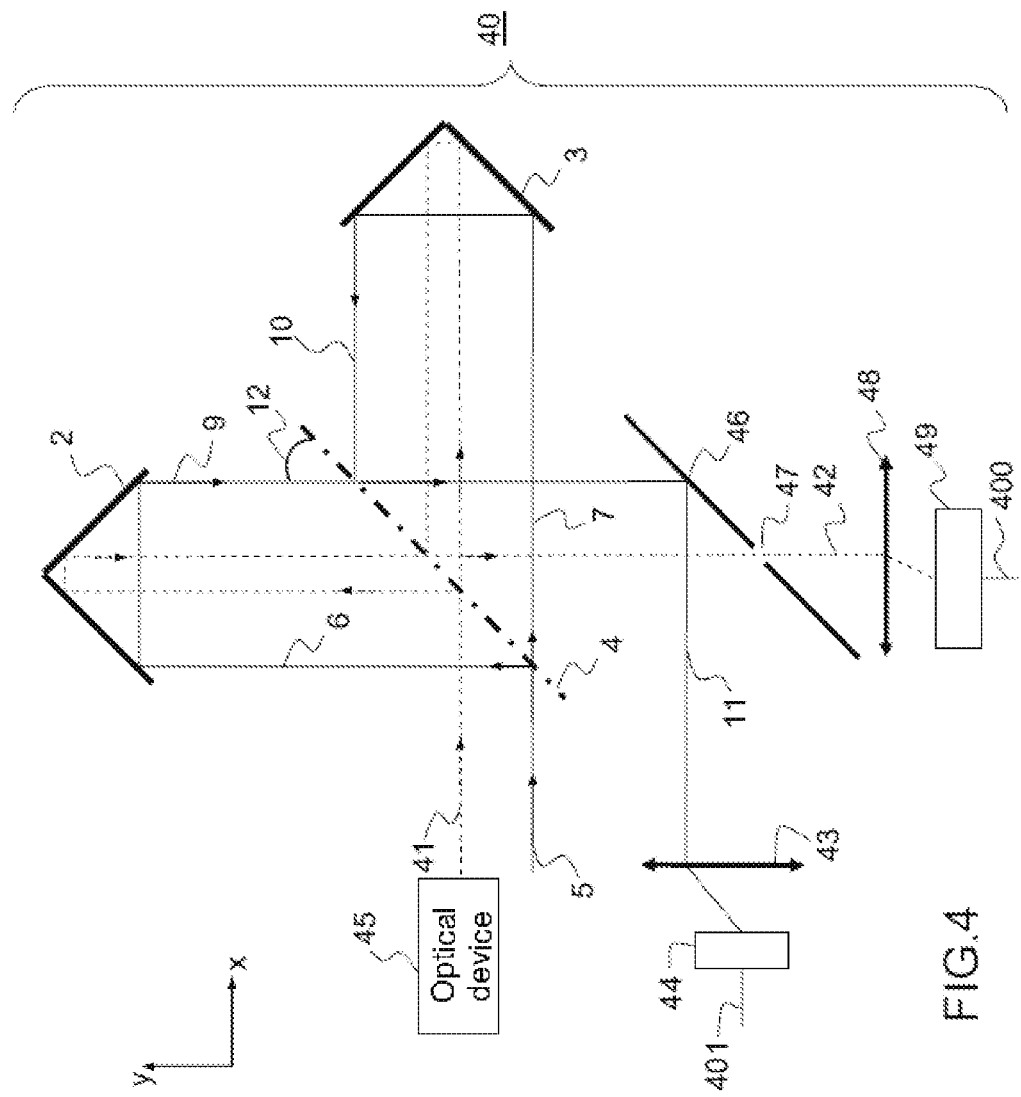
FIG. 4, schematically the first interferometer equipped with a metrology system according to the invention.

FIG. 4 shows schematically a fourth interferometer 40 comprising a metrology system according to the invention. The fourth interferometer 40 shown in FIG. 4 has the same operating principles as the first interferometer 1 shown in FIG. 1. Advantageously, the metrology system according to the invention may also be applicable to various two-arm interferometers using retro projectors, and notably the second and third interferometer 20, 30 shown in FIG. 2 and FIG. 3 respectively. Other examples of interferometers to which the invention can apply are notably described in the following work: "FOURIER TRANSFORM INFRARED SPECTROMETRY", second edition—2007, published by John Wiley and Sons, the authors being Peter R. Griffiths and James A. de Haseth, §5.2 tilt-compensated interferometers pages 112 to 123.

One of the principles of the invention is to use a small number k, equal to or greater than three, of metrology laser beams 41 distributed in the field of view, so as to measure and integrate, in space, the relative displacements between the first and second retroreflectors 3, 2. The laser beams 41 are shown in FIG. 4 by a ray trace 41. If for example, the laser beams 41 are three in number, they may form a trihedron.

An optical device 45, or laser beam injection subsystem 45, is used to inject the k laser beams 41 into the fourth interferometer 40. During its travel through the interferometer, each laser beam 41 may notably pass through a λ/4 plate, or quarter-wave plate, where λ is the wavelength of the laser, making it possible to obtain, using a polarization beam splitter, two laser signals 42 in quadrature per laser beam 41 output by the interferometer 40. In FIG. 4, and for the example, the k laser beams 41 are injected in the same direction as the incoming beam 5. In another embodiment, the k optical beams 41 may be injected into the fourth interferometer 40 for example along the direction of the first beam 6, depending on the construction constraints to which the measurement instrument 40 is subject. A deflecting mirror 46, perforated by small holes 47 may perform a separation at the output of the interferometer between the outgoing science beam 11 and the metrology beam 42 leaving the fourth interferometer 40. The outgoing science beam 11 may be formed from the combination of optical rays entering the measurement instrument, coming from a gaseous component to be analysed, and which have passed through the fourth interferometer 40.

A first converging lens 43 may make the science beam 11 converge on a main detection or capture subsystem 44. The main detection subsystem 44 delivers, as output, interferograms or science signals 401. A science signal represents an item of analogue or digital information resulting from capture at measurement points in the field of view of the fourth interferometer 40. A second converging lens 48 may make the metrology beam 42 converge on a secondary detection subsystem 49. The converging lens 48 and the secondary detection subsystem 49 form parts of a metrology laser beam capture subsystem, hereafter called metrology subsystem. The secondary detection subsystem 49 delivers k laser signals 400 as output.

Figure 5:
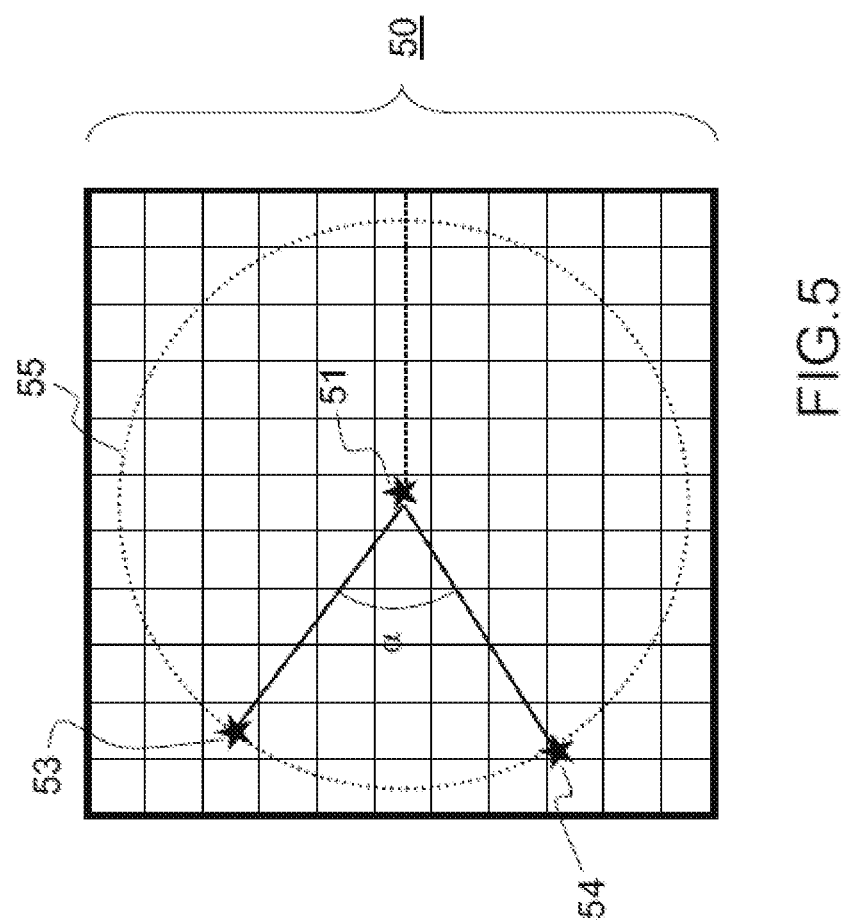
FIG. 5, schematically an example of the arrangement of the laser beams of the metrology device according to the invention.

FIG. 5 shows an example of injection into the fourth interferometer 40 of three laser beams 41, where k is equal to three, in the field of view observed by the interferometer. Each injection position in the field of view corresponds to a unique beam direction. For example the direction of the laser beams 41 in FIG. 4 corresponds to an injection at the centre of the field of view. The field of view observed by the fourth interferometer 40 may be a sample of the space the gaseous content of which it is desired to analyse. The observed field is measured at various measurement points, said measurement points possibly being, for example, arranged in a capture matrix 50, as shown in FIG. 5.

A laser beam 51 is injected along the interferometer axis. For example, in FIGS. 1, 2, 3 and 4, this amounts to injecting the laser beam 51 along the first axis x. A laser beam injected along the interferometer axis has an apparent wavelength which is stable with respect to injection errors.

It is then necessary to add at least two other laser beams to the first laser beam 51 so that the set of injection positions in the field of view of all the lasers are not aligned. For example, second and third laser beams 53, 54 may lie on a circle 55 of radius substantially equal to the observed field. The equidistance of the second and third laser beams 53, 54 from the first beam 51 ensures that no particular direction is preferential, although this is not an absolutely necessary condition. Advantageously, the further apart the laser injection positions, the better the performance of the metrology device according to the invention. The second and third laser beams 53, 54 may be arranged so that there is an angle α of around 60° between a first segment 55 joining the first laser beam 51 to the second laser beam 53 and a second segment joining the first laser beam 31 to the third laser beam 54. The angle α shown in FIG. 5 is cited by way of example; other angles may be used depending on the application, such as for example 90° or an angle of 120°. Advantageously, being able to specify a particular angle helps to improve the performance of the device according to the invention, depending on the various applications thereof.

Figure 6:
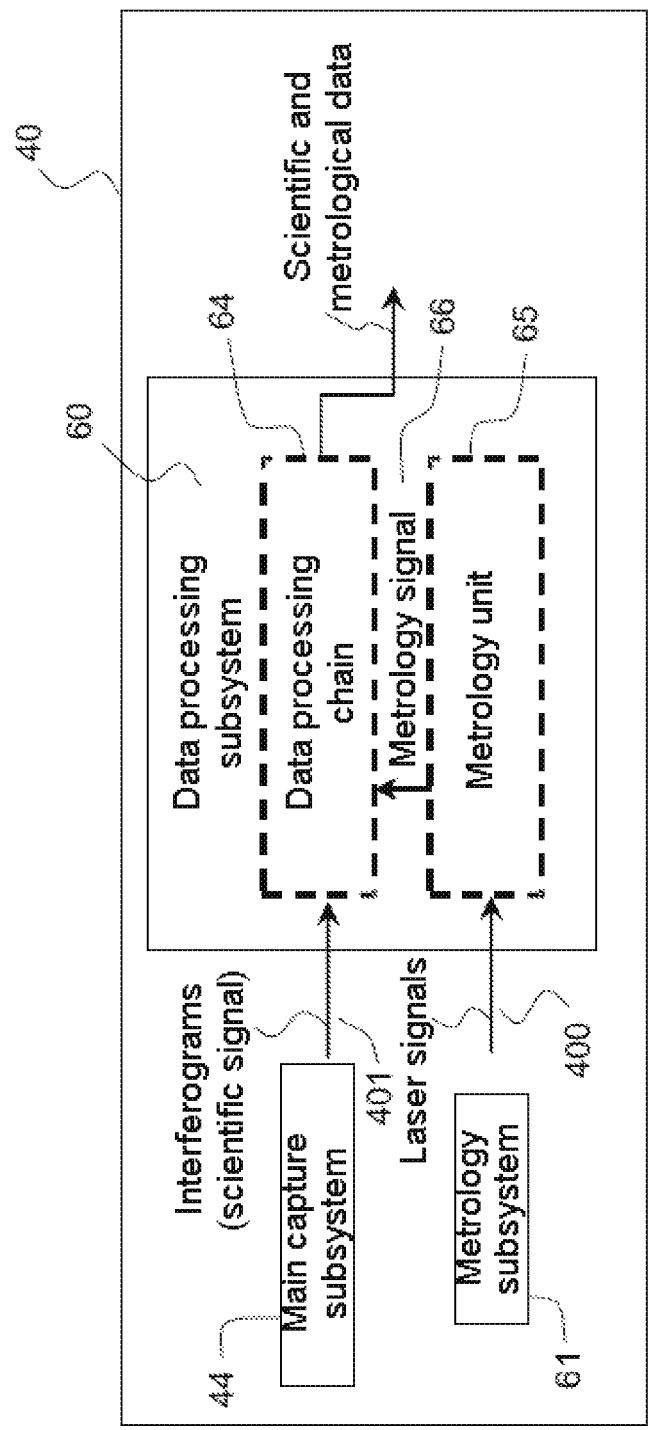
FIG. 6, schematically the measurement device according to the invention.

FIG. 6 shows a data processing subsystem 60 according to the invention. The data processing subsystem 60 may form part of a fourth two-arm interferometer 40 using retroreflectors, as described above. The data processing subsystem 60 serves to process measurement data coming notably from a metrology laser beam capture subsystem 61. The metrology laser beam capture subsystem 61 notably comprises the converging lens 48 and the secondary detection subsystem 49, such as those shown in FIG. 4. The data processing subsystem 60 furthermore makes it possible to process measurement data 401 coming from a main scientific-data capture subsystem 44 as shown in FIG. 4. The metrology subsystem 61 and the main capture subsystem 44 are notably measurement outputs.

The main capture subsystem 44 notably delivers, to a data processing chain 64 forming part of the data processing subsystem 60, scientific interferograms 401 to be studied. In general, an interferogram is a measurement of the interference between two waves.

The metrology subsystem 61 sends, to a metrology unit 65, laser signals 400 representing the measurement of the interference of each laser beam 51, 53, 54, as shown for example in FIG. 5, after they have passed through the interferometer 40. With the aid of the laser signals 400, the metrology unit 65 generates k metrology signals 66, each representing a reference optical path difference. The reference optical path difference may be sent to the data processing chain 64. The data processing chain 64, after preprocessing, delivers, as output, preprocessed scientific data, to be sent to the users of the fourth interferometer 40, and also metrological data.

Figure 7:
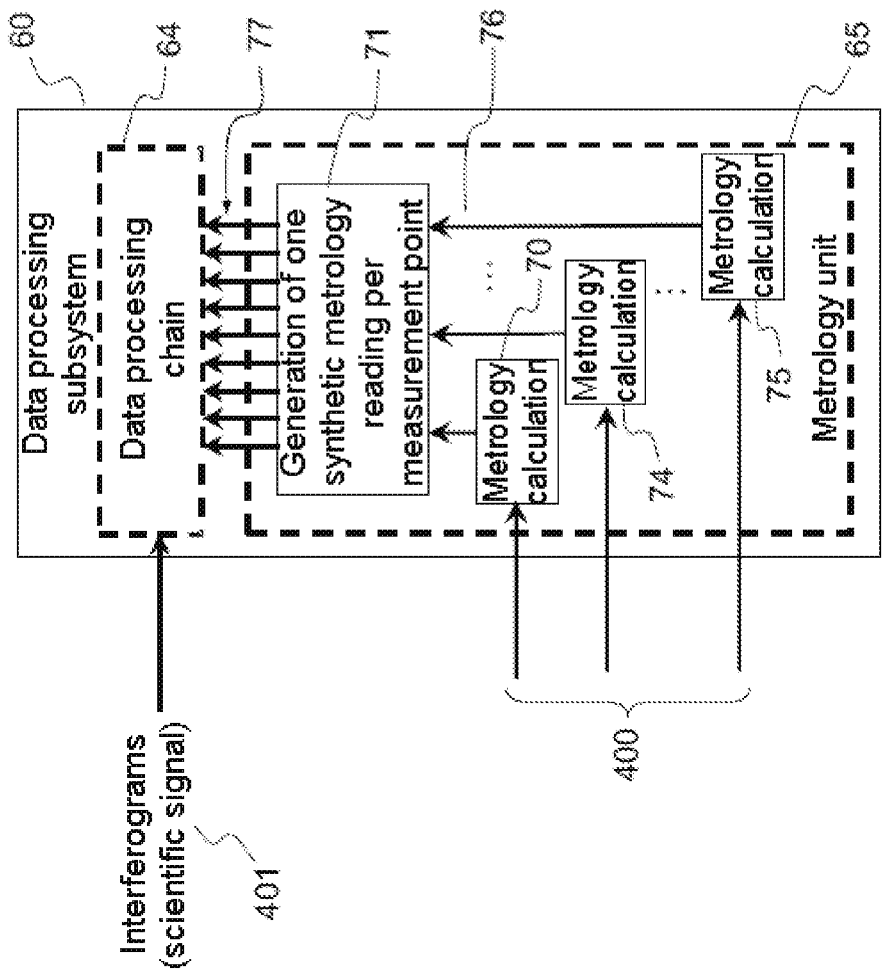
FIG. 7, various steps of the measurement method according to the invention.

FIG. 7 shows schematically several steps of the metrology method according to the invention. FIG. 7 shows notably in greater detail the metrology unit 65, the data processing subsystem 60 and the processing operations carried out.

Arriving as input into the metrology unit 65 are k laser signals, each representing the interference of each laser beam injected into the fourth interferometer 40 and measured after the laser beams 41 have passed through the fourth interferometer 40.

Each laser signal is taken into account by a metrology calculation unit 70, 74, 75 belonging to the metrology unit 65. The processing operations carried out by each metrology calculation unit 70, 74, 75 are independent of one another and will be explained in detail below.

The k metrology calculation units 70, 74, 75 generate k raw metrology signals 76, that is to say k metrology signals estimated for k separate points in the field of view. The k raw metrology signals 76 are used as input to a unit 71 for the generation, or integration of one synthetic metrology reading per measurement point.

The unit 71 for integrating one synthetic metrology reading per measurement point digitally generates synthetic metrology signals 77 for each measurement point, that is to say for each pixel of the matrix 50, shown for example in FIG. 5, in the field of view observed by the interferometer 40. The generated synthetic metrology signals 77 for each measurement point are then delivered to the data processing chain 64.

The data processing chain 64 also receives the scientific interferograms 401, as shown in FIG. 4. The data processing chain 64 may then, depending on the type of interferometer 40 or on the use thereof, perform for example a resampling operation on the scientific interferograms, over a fixed metrology grid, and then perform a Fourier transform on the scientific data or perform a compression by means of a decimation filter, or any other radiometric or spectral calibration processing step.

Figure 8:
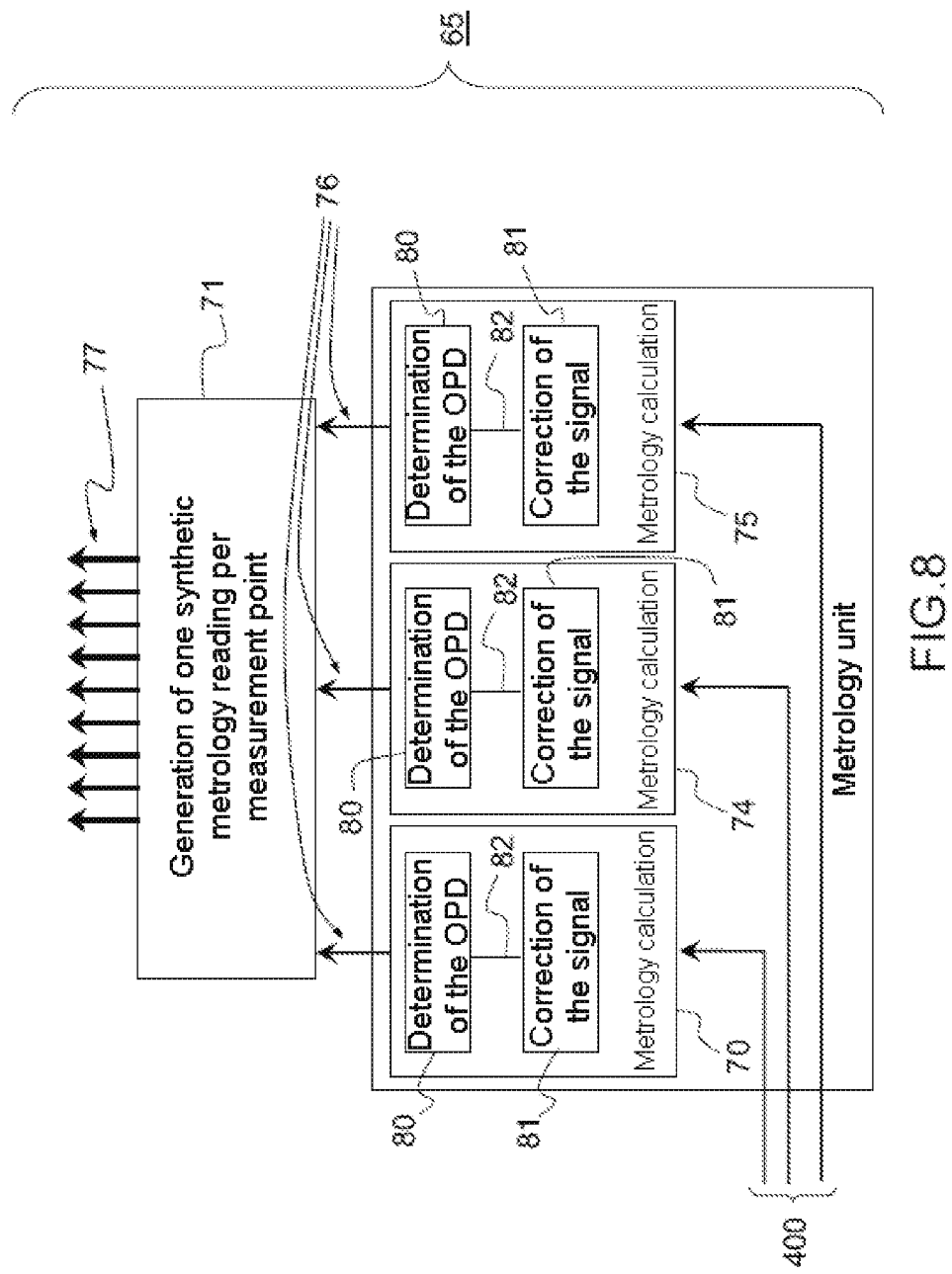
FIG. 8: various steps of the metrology processing of the measurement method according to the invention.

FIG. 8 shows an example of various processing operations that may be carried out by the metrology calculation unit 70, 74, 75 and by the unit 71 for generation of one synthetic metrology reading per measurement point, as shown in FIG. 7.

The processing operations carried out by the metrology calculation units 70, 74, 75 are relatively standard. This step may be carried out on the raw analogue laser signals 400 or after the digitization thereof. For this step, two signals in phase quadrature for each of the k laser beams 400 may be used. The metrology calculation units 70, 74, 75 notably carry out each of the following steps:

a first step of correcting the signal 81, comprising an offset correction, an amplitude correction or a correction for any phase shifts between the signals in phase quadrature; calibration factors may possibly be estimated regularly every n captures, n being an integer to be linked to the stability of the physical phenomenon to be calibrated;

a calculation module (not shown in FIG. 8) is used to determine the number of fringes entirely swept relative to the zero path difference position. The number of fringes may be defined by:

number_of_fringes=whole_part (absolute_raw_metrology_signal/λ)

where λ is the wavelength of the laser.

The number of fringes may for example be set using the Connes' method applied on the scientific signal.

The number of fringes can then be counted on the raw metrology signals 82 after the signal 81 has been corrected;

a second step 80 of determining the optical path difference or OPD of each signal, by applying the arcsine or arcos function, makes it possible to obtain a relative OPD measurement which, when combined with the number of fringes, produces the raw metrology signals 76 corresponding to an absolute OPD: relative_raw_metrology_signal=arcos(corrected_laser_signal) or arcsine(π/2−corrected_laser_signal); and absolute_raw_metrology_signal=number_of_fringes×λ+relative_raw_metrology_signal.

The metrology calculation units 70, 74, 75 therefore deliver, as shown in FIG. 8 for example, k raw metrology signals 76. The k raw metrology signals 76 are then used by the unit 71 for generating one synthetic metrology reading per measurement point in order to calculate the applicable optical path difference at each measurement point, for example in the matrix 50.

Firstly, the integration unit 71 in the field of view estimates a vector, called Apex, that is to say the vector joining the apex of the two corner cubes, 2, 3 of the interferometer 40, said corner cubes 2, 3 both being projected into the same image space. In other words, in FIGS. 1, 2, 3 and 4 the vector Apex is the vector that connects the apex of the retroreflector 3 symmetrically to the apex of the retroreflector 2 with respect to the beam splitter plate 4. The estimation of the vector Apex, explained in detail below, uses k raw metrology signals 76. Next, the linear component of the vector Apex is eliminated. The unit 71 for generating one synthetic metrology reading per measurement point then estimates an optical path difference for each measurement point.

The calculations performed by the unit 71 for generating one synthetic metrology signal per measurement point are explained in detail below.

Let the injection vectors of each of the k laser beams 400 be $\psi L1, \psi L2, \ldots \psi L\kappa$, these forming the following 3×k matrix:

$$\Psi\text{laser}=[\psi L1 \psi L2 \ldots \psi L\kappa] \quad (1000)$$

Let the column vector Apex at each instant t be:

$$CC(t)=[CCx(t) CCy(t) CCz(t)]^T \quad (1001)$$

The optical path difference for each instant 't' is given by the following equation:

$$\text{OPDlaser}(t)=2\times CCT(t)\times\Psi\text{laser} \quad (1002)$$

in which $$\text{OPDlaser}(t)=[\text{OPDlaser1}(t) \text{OPDlaser2}(t) \ldots \text{OPDlaser}k(t)]^T \quad (1003)$$

where OPDlaser1($t$), OPDlaser2($t$), ..., OPDlaser$k$($t$) represent the optical path differences of the k laser beams 400 respectively. Furthermore, the metrology calculation unit 70 produces and delivers a measurement row vector:

$$mOPDlaser(t)=[mOPDlaser1(t) mOPDlaser2(t) \ldots mOPDlaserk(t)] \quad (1004)$$

Using equation (1002), it is possible to estimate the vector Apex given by the following equation:

$$eCC(t)=0.5 \times mOPDlaser(t) \times [e\Psi laser]^{-1} \quad (1005)$$

in which $e\Psi laser$ is an estimate of $\Psi laser$ and $[e\Psi laser]^{-1}$ is the pseudo-inverse of $e\Psi laser$.

Next, the linear component of eCC is extracted using the following equation:

$$eCCcor(t)=eCC(t)-eCCx(t)*[0eCentreOfFringesY \; eCentreOfFringesZ] \quad (1006)$$

in which [eCentreOfFringesY eCentreOfFringesZ] is an estimate of the angular coordinates of the centre of the fringes. This estimate may be made for example by a linear regression on the vector CC(t).

Let $\psi P1, \psi P2, \ldots$ and $\psi PN$ be the field position vectors or the angular coordinates of N measurement points in the field of view of the interferometer 40, for example forming the following 3×N matrix:

$$\Psi sounding=[\psi P1 \; \psi P2 \ldots \psi PN] \quad (1007)$$

Therefore using equations (1002) and (1005), the metrology signal for each sounding point at a time T is estimated by:

$$eOPDsounding(t)=2 \times eCCcor(t) \times e\Psi sounding \quad (1008)$$

Thus, a metrology reading is obtained at each measurement point in the field of view.

Advantages

One of the advantages of the invention is to generate a metrology reading which integrates the path in space of the movable elements of the interferometer and thus makes it possible to compensate for the defects thereof. In fact, the metrology system according to the invention generates differences in the path lengths of the laser signals in the field of the interferometer integrating any drift or vibration of the mechanism for displacing the movable element(s) of the interferometer. The system according to the invention is also robust with respect to any drift in the injection angles of the lasers.

Advantageously, the metrology system according to the invention makes it possible to correct all the components of the path error: path offset, parabolic component, vibratory effect.

The system according to the invention notably makes it possible to maintain an apparent laser wavelength which is stable with respect to the laser injection.

The invention also has the advantage of being able to incorporate compensation for a drum skin effect of the beam splitter plate.

Advantageously, the method according to the invention comprises relatively uncomplicated digital processing operations allowing real-time processing of the signals.

The use of the metrology system according to the invention in an interferometer makes it possible to achieve a very high precision in the interferometer measurements with unlimited bandwidth and no delay.

The invention claimed is:

1. A metrology system applied to an interferometer for remotely analysing a gaseous compound by Fourier transform spectroscopy, said interferometer being a two-arm interferometer, comprising at least one movable retroreflector, the metrology system comprising:

a laser device configured to inject at least three metrology laser beams input into the interferometer;

a capture subsystem for receiving at least three metrology laser beams output by the interferometer, said capture subsystem delivering at least three laser signals each representing a measurement of an interference of one of the metrology laser beams after passing through the interferometer;

at least one metrology unit which, from one or more of the at least three laser signals, generates synthetic metrology signals for various points in a field of view of the interferometer, the synthetic metrology signals thus generated taking into account a path of the at least one movable retroreflector in space and said metrology unit including a metrology calculation component which estimates, for each received laser beam, absolute optical path differences, said at least one metrology unit including three metrology calculation units each calculating a raw metrology signal from a corresponding laser signal; and a unit configured to generate one synthetic metrology reading per measurement point, and to generate, from at least three raw metrology signals, one synthetic metrology signal per measurement point in the field of view of the interferometer, wherein the unit is configured to perform at least the following processing steps:

an estimation of a vector apex joining the positions of the vertices of the at least one movable retroreflector, an elimination of the linear component of the vector apex; and a generation of an optical path difference represented by a synthetic metrology signal, at different points in the field of view, from the vector apex and from the angular coordinates of the various points in the field of view.

2. The metrology system according to claim 1, wherein the injection subsystem injects at least three laser beams, one of the three laser beams being injected into the centre of the field of view of the interferometer.

3. The metrology system according to claim 1, wherein the metrology calculation unit performs at least the following processing steps:

a correction of the laser signal: correction of the differences in amplitude, phase and offset;

a determination of a path difference associated with the laser signal.

4. A method of metrology applied to an interferometer for remotely analysing a gaseous compound by Fourier transform spectroscopy, said interferometer being a two-arm interferometer, including at least one movable retroreflector, the method comprising:

a step of injecting at least three metrology laser beams input into the interferometer, performed by a laser device;

a step of receiving at least three metrology laser beams output by the interferometer, performed by a capture subsystem;

a step of generating at least three laser signals, each representing a measurement of an interference of a metrology laser beam after passing through the interferometer, performed by the capture subsystem and a step of generating synthetic metrology signals by at least one metrology unit from one or more of the at least three laser signals for various points in a field of view of the interferometer, the synthetic metrology signals thus generated taking into account a path of the at least one movable retroreflector in space, the step of generating said synthetic metrology signals comprising an estimation, for each received laser beam of absolute optical path differences, performed by a metrology calculation component forming part of the metrology unit, a calculation of a raw metrology signal from a laser signal by each of three metrology calculation units that form parts of the metrology unit, a generation, from at least three raw metrology signals, of one synthetic metrology signal per measurement point in the field of view of the interferometer, by a unit for the generation of one synthetic metrology reading per measurement point, the generation of the one synthetic metrology reading per measurement point further comprising:

an estimation of a vector apex joining the positions of the vertices of the at least one movable retroreflector, an elimination of the linear component of the vector apex, and a generation of an optical path difference represented by a synthetic metrology signal, at different points in the field of view, from the vector apex and from the angular coordinates of the various points in the field of view.

5. The method according to claim 4, wherein one of the three laser beams is injected into the centre of the field of view of the interferometer.

6. The method of metrology according to claim 4, he calculation of a raw metrology signal further comprising:

a correction of the laser signal: correction of the differences in amplitudes, phase and offset; and a determination of a path difference associated with the laser signal.

\* \* \* \* \*